(12) United States Patent
McAdams

(10) Patent No.: US 7,945,302 B2
(45) Date of Patent: May 17, 2011

(54) WOUND MAPPING SYSTEM

(75) Inventor: Eric Thomas McAdams, Whitehead (GB)

(73) Assignee: University of Ulster, Co. Londonderry (GB)

( * ) Notice: Subject to any disclaimer, the term of this patent is extended or adjusted under 35 U.S.C. 154(b) by 970 days.

(21) Appl. No.: 10/537,535

(22) PCT Filed: Dec. 5, 2003

(86) PCT No.: PCT/IB03/06399
§ 371 (c)(1),
(2), (4) Date: Jun. 3, 2005

(87) PCT Pub. No.: WO2004/049937
PCT Pub. Date: Jun. 17, 2004

(65) Prior Publication Data
US 2006/0270942 A1   Nov. 30, 2006

(30) Foreign Application Priority Data
Dec. 5, 2002   (GB) .................................. 0228375.2

(51) Int. Cl.
*A61B 5/04* (2006.01)
(52) U.S. Cl. ........................................ 600/382; 600/547

(58) Field of Classification Search .................. 600/547, 600/372, 393
See application file for complete search history.

(56) References Cited

U.S. PATENT DOCUMENTS

| | | | | |
|---|---|---|---|---|
| 5,181,905 A * | 1/1993 | Flam | ............................... | 602/41 |
| 5,184,620 A * | 2/1993 | Cudahy et al. | ................ | 600/382 |
| 6,055,448 A | 4/2000 | Dempsey et al. | | |
| 6,308,097 B1 * | 10/2001 | Pearlman | ....................... | 600/547 |
| 6,788,966 B2 * | 9/2004 | Kenan et al. | ................... | 600/372 |
| 6,963,772 B2 * | 11/2005 | Bloom et al. | ................... | 600/547 |
| 2002/0082668 A1 | 6/2002 | Ingman | | |
| 2003/0176808 A1* | 9/2003 | Masuo | .......................... | 600/547 |
| 2003/0199783 A1 | 10/2003 | Bloom et al. | | |

OTHER PUBLICATIONS

International Search Report mailed May 11, 2004 for International Patent Application No. PCT/IB03/06399 filed Dec. 5, 2003, 3 pages.

* cited by examiner

*Primary Examiner* — Max Hindenburg
*Assistant Examiner* — Renee Danega
(74) *Attorney, Agent, or Firm* — Morrison & Foerster LLP

(57) ABSTRACT

A tissue mapping system comprising a two dimensional array of test electrodes 10 for application to the surface of tissue under investigation and circuit means 50-66 for measuring an electrical characteristic of the tissue underlying each test electrode. In one embodiment the electrical characteristics is the impedance of the tissue underlying each test electrode.

20 Claims, 5 Drawing Sheets

WOUND MAPPING SYSTEM

CROSS-REFERENCE TO RELATED APPLICATIONS

This application is a U.S. NATIONAL PHASE application of International Application No. PCT/IB03/006399, filed Dec. 5, 2003, which claims priority, under the Paris Convention, to GB 0228375.2 filed on Dec. 5, 2002. All of which are hereby incorporated by reference in their entirety.

This invention relates to a system and method for mapping tissue, especially but not limited to the mapping of a skin wound.

Wound measurement appears to be the only method clinicians have in determining the state of a wound or to assess the effectiveness of a given treatment or dressing, indeed it has been reported that in clinical trials, wound area is the most commonly reported property of wounds[1]. Although current methods are numerous, almost all are simple and most are subjective, bringing their accuracy into question.

The most frequently used techniques are two-dimensional and include linear measurements, wound tracing, planimetry, and stereophotogrammetry.

Linear measurements are perhaps the most simple and involve length and width measurements, taken at the longest length of the wound and the widest width, measured perpendicular to the length axis[2] using a wound gauge or ruler. While clearly quick and inexpensive this method is very subjective and will therefore result in a certain degree of inaccuracy.

A second linear measurement often used in the assessment of wounds is that of area. Several manufacturers to the health care industry have produced a gauge with concentric circles which can be used to estimate wound area. However, as very few wounds will be perfectly circular this method will introduce a large amount of error into the result. Even in cases where symmetry is evident, subjective identification of the wound boundary can cause inaccuracies in this method.

Planimetry, wound tracing or the acetate method is the technique which employs the use of metric graph paper with a 4 cm grid size where the complete squares within the traced wound area are counted and the result indicated in square centimetres[2].

A further 2-dimensional technique used to determine wound parameters is that of stereophotogrammetry, a more complex and expensive method involving the use of a video camera attached to a computer with appropriate software. The wound is captured on video after a target plate has been placed on the plane of the affected area. The target plate allows correct orientation and distortion correction in order to obtain a true image of the wound before it is downloaded to the computer. The wound area can then be traced from the displayed image and the software calculates the wound length, width and area[2]. The improved accuracy of this method and the ability to record results in a database makes it more advantageous than previous techniques but its expense is a limitation.

While a study by Kantor[1] suggests that these methods are adequate in determining wound parameters, the need to remove dressings and bandages in order to obtain the measurements remains a crucial shortfall. While there is an obvious necessity to renew and replace dressings from a health point of view, the frequency of replacement can have an effect on the state of the wound. Continual agitation of the wound area does not encourage healing and removal of adhesive dressings can serve to disrupt the formation of new tissue. Therefore it would be desirable to develop a method of wound measurement which did not require the removal of dressings to calculate the chosen parameters.

An accurate, atraumatic mapping technique would have the very attractive advantage of enabling scientific assessment of the efficacy of various treatments claimed to promote/enhance wound healing and the unequivocal identification of those most effective.

The skin has several functions including temperature regulation, immunity and protection and when the integrity of the skin is comprised by trauma it is said to be wounded.

Wounds vary in severity and this is gauged mainly by the depth or penetration of the injury and the skin layers involved. Minor abrasions where the portion of skin lost does not extend beyond the epidermis into the dermis is defined as an epidermal wound, while deep wounds are injuries where substantial tissue loss is evident into the lower dermal layers.

The skin's ability to replace itself goes some way to explaining the definition of wound healing. The CREST guidelines on 'Principles of Caring for Patients with Wounds', published in 1998 defines healing in the pathological context, as '... the body's replacement of destroyed tissue by living tissue[3]. The onset of an injury triggers a series of cellular and biochemical events from the biological and immunological systems whereby an organised pathway of processes results in a healed wound.

The healing process can be divided into 4 sequential but not distinct phases, haemostasis, inflammation, proliferation and maturation. Haemostasis is the process of stopping bleeding[4] which is a common occurrence in deep tissue trauma; following injury a discharge of blood or fluid from a vessel in the surrounding tissue (extravasation) initiates blood clotting and platelet activation. It is this platelet activation which triggers haemostasis, vasoconstriction and new tissue formation to aid in wound repair. The vasoconstriction is a result of the release of a series of chemical mediators such as histamine, serotonin and adenosine triphosphate (ATP). Their role is to attract the circulating leucocytes (colourless blood component which protects against micro organisms) to the site of impact[4]. The onset of vasoconstriction also coincides with the start of the second or inflammatory phase.

The increased volume of 'local' blood allows plasma to leak to the surrounding tissue thus swelling them, hence inflammation. Neutrophils and monocytes arrive at the wound dormant and on activation the neutrophils set about removing any offensive bacteria while the monocytes become macrophages producing growth factors to accelerate the healing process. Macrophages themselves also phagocytose pathogenic organisms and clear tissue debris. The last stage of this phase sees the released growth factors stimulating endothelium to oversee the growth of newly formed blood vessels.

The third stage, the proliferation phase is the growth and reproduction of tissue, namely connective or granulation tissue whose formation is dependent on the newly formed blood vessels. The blood vessels provide a suitable environment for tissue regeneration by providing nutrients and oxygen for the cells. Firstly fibroblasts create a network of collagen fibres in the wound bed and produce a sticky substance, proteoglycan which fills the tissue bed binding the fibres together to form a stable framework. Epithelialisation and contraction are the final processes in this stage whereby the wound regenerates epithelium from the outer edges of the wound towards the centre. The cells migrate across the surface to they meet and at the same time the wound is contracted by myofibroblasts.

The fourth and final phase of the healing process is the maturation phase which can be several weeks from the time of injury and involves the remodelling of the collagen fibres laid down in the proliferation phase[4]. This collagen is soft and gelatinous and is replaced in this stage by more orderly and stronger collagen. The final act in the healing process is the removal of fibroblasts from the wound site and the restructuring of blood vessels away from the area which results in the shrinking and paling of the scar tissue[4].

The skin is made up of 3 main layers:—the subcutaneous layer, the dermis, and the epidermis (the strongest layer)[5].

The epidermis, the outermost layer, is in direct contact with the environment and therefore provides a protection barrier to outside materials (products, water, etc.) as well as filtering sunlight. Unlike any other organ of the body, the epidermis is self-renewing and hence replaces itself continually[6].

The epidermis can be sub-divided into several further layers with the stratum corneum forming the outermost layer. Cells in the underlying basal layer are constantly multiplying and undergo changes as they push up towards the skin's surface. As these cells become flattened, compacted and dehydrated, they lose their nuclei and develop a hardening protein, eventually forming the stratum corneum. The dead cells on the surface are continuously being shed, replaced by the cells migrating from the underlying layers[7].

The stratum corneum consists of several layers of dead cells and varies in thickness depending on location on the body, the thickest layers being on the palms of the hand and the bottom of the feet. The stratum corneum becomes thicker with age and exposure to the elements making it more susceptible to wrinkles and creases[5].

The relatively non-conductive stratum corneum sandwiched between a conductive electrode interface and the conductive hydrated underlying tissue acts as a dielectric between two plates as in a capacitor. Therefore the stratum corneum's electrical properties is often represented by a simple capacitor, $C_P$[8].

Some ions do however traverse the stratum corneum barrier and this is represented, along with the capacitance, by a large parallel resistance, $R_P$.

The tissues underlying the skin are conductive and can be represented by a resistance, $R_T$, in series with the above parallel combinations. The equivalent circuit model is shown in FIG. 1. This equivalent circuit model comprising simple resistances and a capacitance is obviously a simplification of the skin's complex electrical properties.

At very high frequencies, the impedance of the capacitance tends to zero and the overall impedance approaches that of $R_T$. At low frequency the impedance of the capacitance tends to infinity and current therefore flows through the series combination of $R_T$ and $R_P$ and the overall impedance is generally therefore much larger than the high frequency case.

Theoretically the impedance locus of the 'classical' model (equivalent circuit incorporating a resistance and capacitance in parallel) should consist of a semi-circular arc whose centre is located exactly on the real axis, as shown on FIG. 2.

However, FIG. 3 shows the typical form of a measured impedance locus plot of the electrode-skin interface, demonstrating that the simple model described above is not adequate to fully characterise the electrical properties of the skin.

$R_{inf}$ and $R_o$, the intercepts with the real axis at high and low frequencies respectively, are the high and low frequency limit resistances. The depression of the centre of the arc below the axis, is expressed in terms of the angle $\phi$. $\omega_o$ ($=2\pi f_o$) is the angular velocity of the 'peak' of the arc. This is the point with the largest value of reactance, $X_S$[6].

Impedance loci such as the one above have been found to be well modelled by the formula derived by Cole in 1940[10] (equation1). [Other mathematical models are possible].

$$Z = R_\infty + (R_0 - R_\infty)/[1 + j\omega/\omega_0)^\alpha] \quad (1)$$

The expression is used to describe the complex impedance of certain biological tissues. $\alpha$ is dimensionless and has a value $0 < \alpha \leq 1$ and is related to $\phi$ such that $\phi = \alpha\pi/2$. When $\alpha = 1$, the impedance locus is a semi-circular arc whose centre lies on the real axis with a frequency intercept angle $\phi$ of 90°. When $\alpha < 1$, as is normally the case, the locus takes the form of a 'depressed' semi-circular arc whose centre lies below the real axis and the frequency intercept angle $\phi$ is less than 90°.

The complex impedance described by the Cole equation (1) corresponds to several equivalent circuits. FIG. 4 shows one such circuit.

$Z_{cpa}$ is an empirical, constant phase angle impedance which shunts the resistance $R_p$ where:

$$Z_{cpa} = K(j\omega)^{-\alpha} \quad (2)$$

K is a measure of the magnitude of $Z_{CPA}$ (i.e. $K = |Z_{CPA}|_{\omega=1}$) and has units of $\Omega s^{-\alpha}$. These circuit elements can be expressed in terms of the Cole parameters $R_\infty$, $R_0$, $\omega_0$ and $\alpha$, as follows:

$$R_p = (R_0 - R_\infty) \quad (3)$$

$$K = (R_0 - R_\infty)/T_0^\alpha = Rp/T^\alpha. \quad (4)$$

$$R_T = R_\infty \quad (5)$$

It can be readily appreciated that when the stratum corneum at a given skin site is punctured, abraded or absent (as a consequence of trauma or disease, for example) the measured low-frequency impedance at the site will be dramatically reduced due the absence of the large stratum corneum impedance (represented in the simplest case (FIG. 1) by the parallel combination of the skin's capacitance and resistance, $C_P$ and $R_P$). Only the small resistance, $R_T$, of the underlying tissue will remain.

Mapping, for example, the low-frequency impedance of skin sites in and around a wound site will evidence clearly the major differences between healthy skin (high impedance) and the wound (low impedance).

It is therefore an object of the invention to provide an improved system and method of mapping tissue, in particular but not exclusively skin wounds.

Accordingly, the present invention provides a tissue mapping system comprising a set of test electrodes for application to the surface of tissue under investigation and circuit means for measuring an electrical characteristic of the tissue underlying each test electrode.

Preferably the system further includes means for displaying said measured characteristics and/or derivative(s) thereof in human-readable form.

Preferably, too, the electrical characteristic is the impedance of the tissue underlying each test electrode.

The invention further provides a method of mapping tissue comprising applying a set of test electrodes to the surface of tissue under investigation and measuring an electrical characteristic of the tissue underlying each test electrode.

The invention further provides a wound dressing incorporating a set of test electrodes for application to the surface of wound tissue and circuit means for measuring an electrical characteristic of the tissue underlying each test electrode.

An embodiment of the invention involves the use of a 'smart' wound dressing which can be used to monitor the skin's electrical impedance and thus to assess the size, shape, depth and composition of the wound, all without the need of removing the dressing. The principle of this embodiment is illustrated diagrammatically in FIG. 5, where the electrode connecting leads are omitted for clarity.

If an array of test electrodes 10, incorporated in a wound dressing 12, is located over a wound site 14 in intact skin 16, the individual impedances of the tissue underlying each test electrode 10 can be used to create a two-dimensional map of the wound. If a sufficient number of small area electrodes are used, the shape and size of the wound can be ascertained from the measured impedance values. Over time, changes in the wound shape and size can be followed using this technique.

It is possible to model the electrical properties of tissues with equivalent electrical circuits. With the correct choice of mathematical or equivalent circuit model, it is possible to relate the model elements to the underlying physical processes and thus study the healing processes and meaningfully assess the efficacy of a range of therapies.

The use of a multi-electrode array enables the monitoring of different sites without the need to move a single electrode from one measurement site to the next.

Hydrogel is presently used as a wound dressing as it protects the wound bed from foreign contaminants, and hydrates and enhances the environment essential to thorough wound healing. Hydrogels can also be used in the construction of bio-impedance monitoring electrodes and, along with the use of screen printing or similar technologies, lend themselves to the fabrication of accurate, flexible, low-profile electrode arrays. The test electrodes can therefore be incorporated into a hydrogel-based wound dressing and used to monitor the wound and the effect of therapy without the need to remove the dressing. A significant improvement on current techniques is that this system does not interfere with the wound bed. As the preferred embodiment is designed to be used as part of, or to constitute, the wound dressing, it allows new tissue formed as part of the healing process, to remain undisturbed while the wound is being assessed. In addition to calculating the wound area, this device is also effectively assisting wound healing.

Most of the prior art discussed above produce wound parameters like length and width and at best volume values, but none, with the exception of the stereophotogrammetry, produce a map or picture of the wound. Even using stereophotogrammetry the wound parameters must be calculated from the picture after the wound photograph has been 'traced' around using the computer. This method can be inaccurate due to the difficulties associated with capturing a real size image of the wound to download.

In one embodiment, the invention maps the wound direct from the site and produces an image, complete with calculations of area, tissue type etc., on a computer screen with little involvement from the clinician required, therefore reducing subjectivity and error.

As a wound heals, particularly a full thickness wound, it passes through several phases or stages where new tissue and eventually skin will form. Therefore another indication of wound healing is the tissue type present in the wound bed. It is possible to model the electrical properties of tissues with mathematical and/or equivalent electrical circuits. With the correct choice of mathematical or equivalent circuit model, it is possible to relate the model elements to the underlying physical processes and thus study the healing processes and meaningfully assess the efficacy of a range of therapies.

The invention therefore allows a clinician to characterise tissue and hence evaluates the tissue type present under the individual electrodes incorporated in the dressing. This information can then be used to establish the state of the wound.

Due to the severity of some full thickness wounds, many sores will not heal without some form of intervention. Several treatment techniques are employed the use of drugs, wound dressings and the application of electrical signals. Any affect that these techniques have on wound healing can ideally be assessed using electrical impedance spectroscopy (EIS). The application of electrical fields (DC, pulsed, etc.) has been reported to promote wound healing[11,12,13]. Unfortunately, due to the difficulties in assessing wound healing, it has not been possible to establish clearly the best 'electrical therapy'. This shortcoming can be addressed with the use of the impedance array as the test electrodes can be used to apply the desired 'electrotherapeutic' signals and to evaluate their effects, all without removing the dressing. The test electrodes can also be used for iontophoretic drug delivery and assessment of resultant therapeutic effect or tissue trauma.

An embodiment of the invention will now be described, by way of example, with reference to the accompanying drawings, in which.

Figure 7:
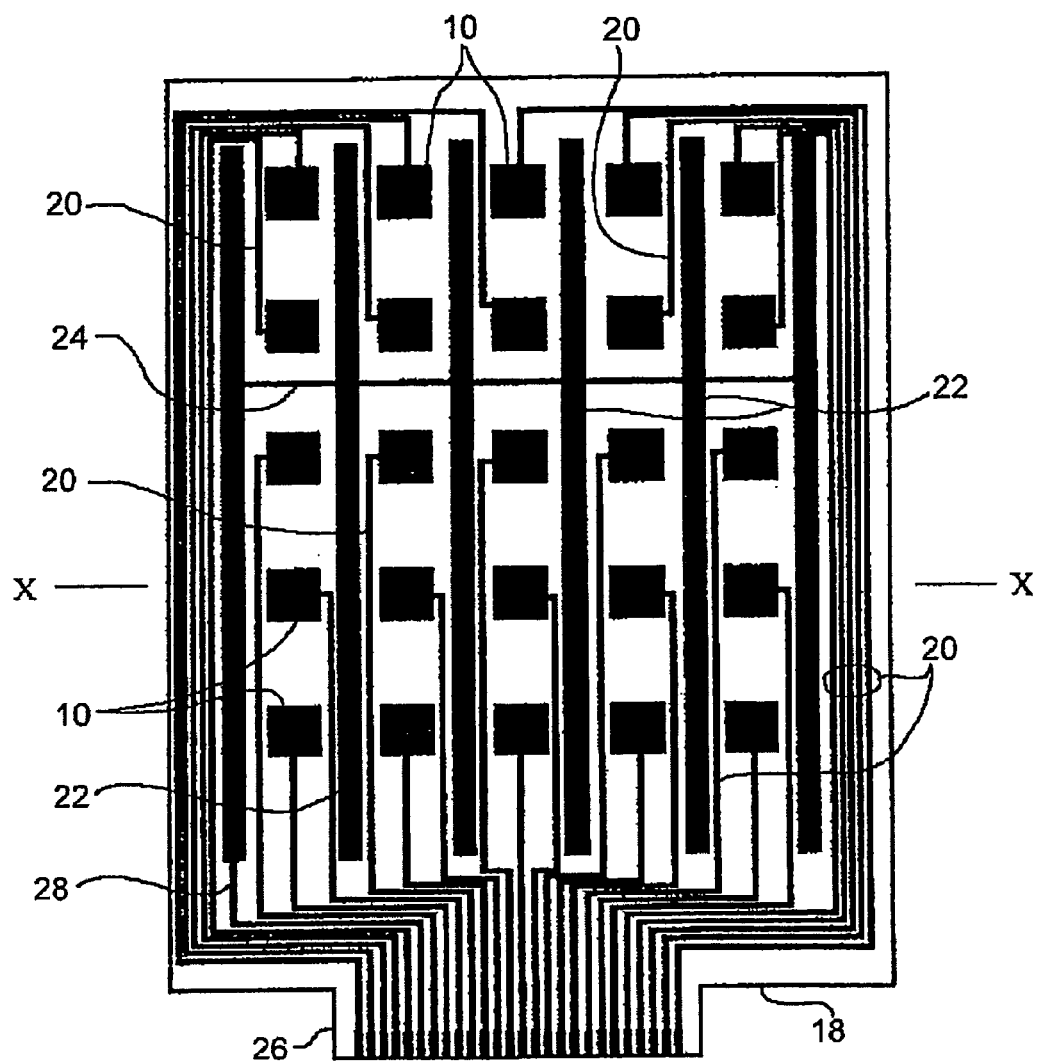
FIG. 7 is a plan view of a 5×5 rectangular array of test electrodes used in an embodiment of the invention.
Figure 8:
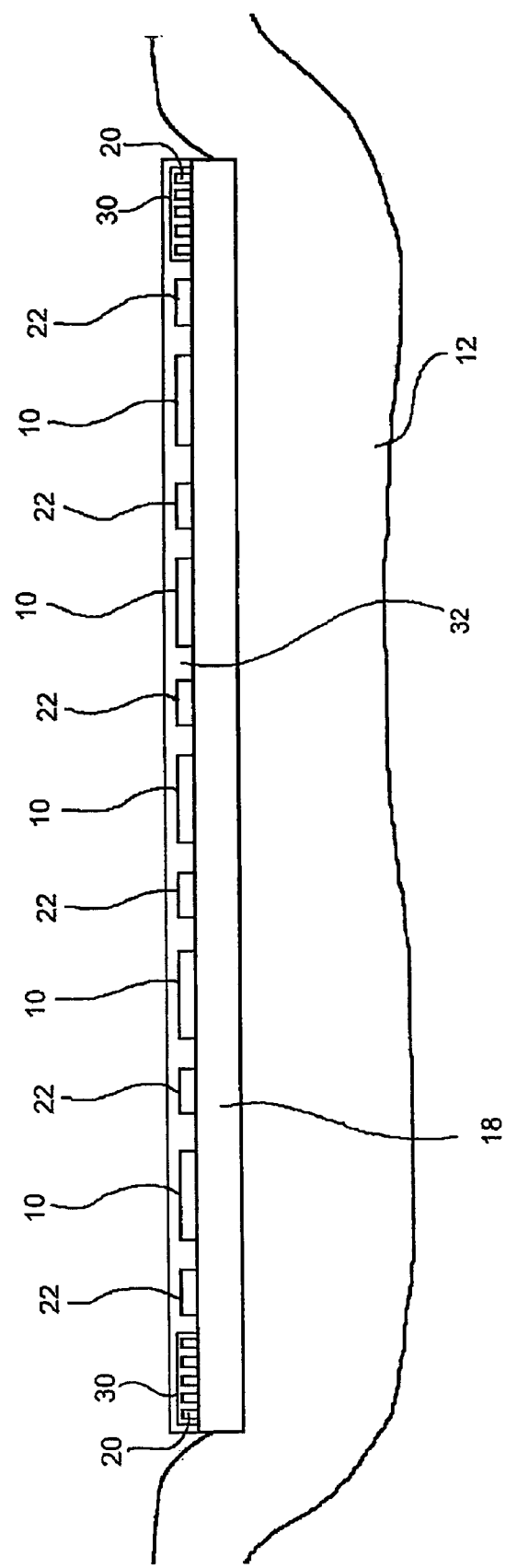
FIG. 8 is a cross-section through the array of test electrodes taken on the line X-X of FIG. 7, the array being incorporated in a wound dressing.

Referring first to FIGS. 7 and 8, a rectangular 5×5 array of test electrodes 10 is screen printed onto a thin flexible insulating substrate 18, each test electrode 10 having a respective lead 20 also screen printed on the substrate. Screen printing enables the accurate patterning and positioning of the electrodes and their associated leads. The leads 20 are preferably formed using a conductive material such as a serigraphic silver-loaded ink (e.g. PF-410 silver conductive ink from Norcote, England) and the test electrodes 10 are preferably formed using a serigraphic silver/silver chloride-loaded ink to ensure good electrical performance at the electrode-gel interface (e.g. Part No. 5874 from Dupont, Bristol, England). Other materials may be used if the electrodes are also to be used apply iontophoretic or other therapeutic electrical signals as will be described. All twenty-five test electrode leads 20 are brought together at a projecting connector edge 26 of the substrate 18.

A number of reference electrodes 22 are also screen printed on the substrate 18. In the present case six substantially parallel strip-like reference electrodes 22 are provided, four of which extend each between a respective pair of adjacent columns of five test electrodes 10 and two more of which are applied on the outsides of the test electrode array. The six reference electrodes 22 are connected together in common by a cross lead 24, and a single further lead 28 connects all the reference electrodes 22 to the connector edge 26.

Figure 9:
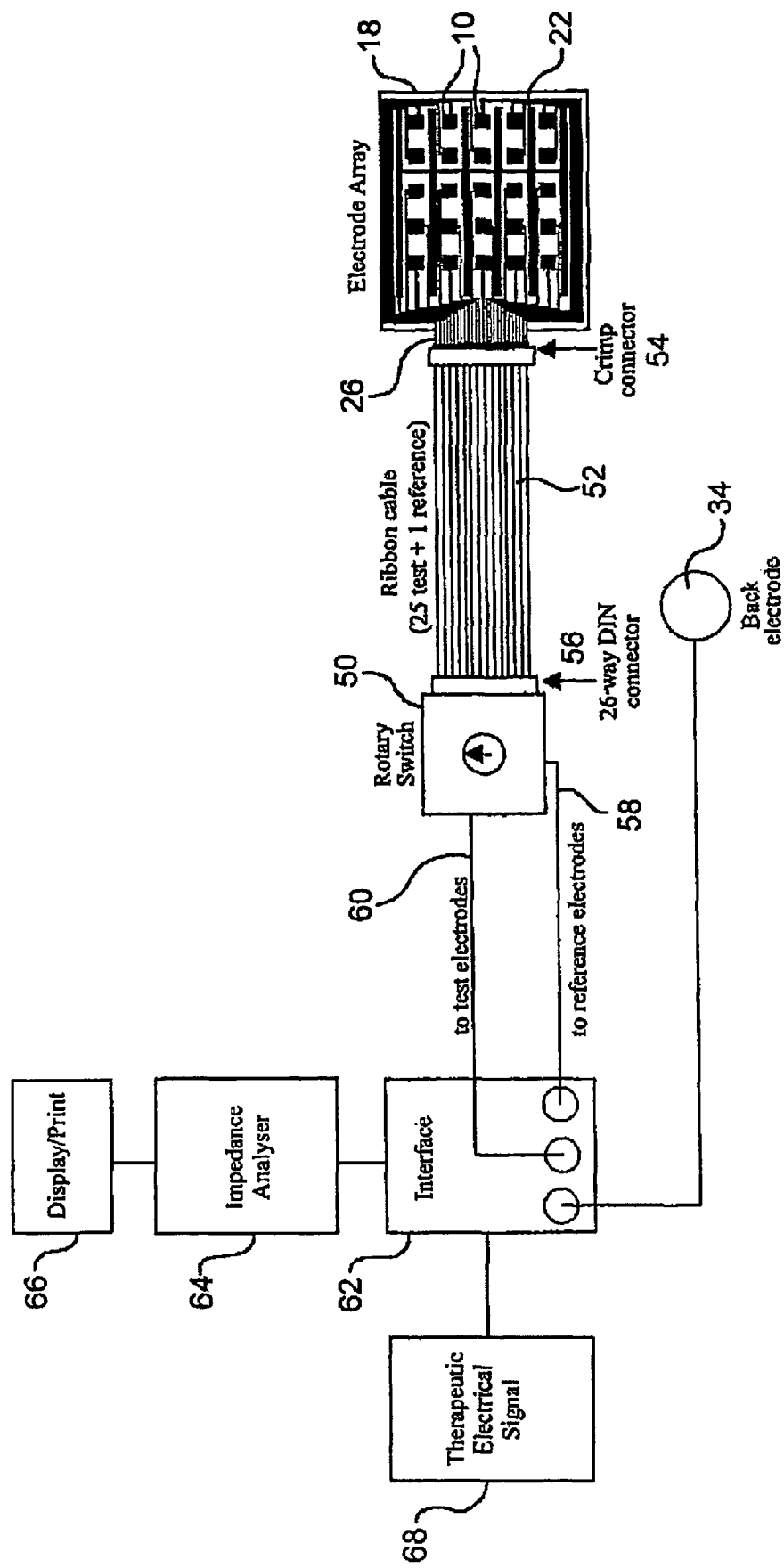
FIG. 9 is a block diagram of a wound mapping system using the array of FIG. 7.

An insulating layer 30 (FIG. 8) is deposited on each lead 20, 24 and 28 to avoid electrical shorting (e.g. dielectric ink SD2460 Flex Komp A & B from Norcote, England). However, several millimetres of each lead 20, 28 is exposed at the connector edge 26 for connection to drive circuitry (FIG. 9). The substrate 18 may be CT4 heat stabilised polyester substrate from Autotype, Wantage, England. The substrate 18 is incorporated in a wound dressing 12.

The substrate 18 can be one continuous sheet or be perforated or cut into 'finger-like' peninsulas to enhance flexibility and enable moisture to escape where necessary. A backing of suitable material (e.g. 1.6 mm adhesive foam, 8104/800C from Medifix, Luton, England) can be used, if necessary, to hold the 'finger-like' peninsulas together and ease application.

A hydrogel layer 32 is used as an electrode gel as hydrogels are well tolerated by the skin and are currently used in wound dressings (e.g. SW 200 or SW 206 hydrogels from First Water, Ramsbury, England). A single sheet of hydrogel 32 can be used to cover all the test and reference electrodes 10, 22 and their leads, as shown in FIG. 8, or individual hydrogel 'pads' can be placed over each test and reference electrode. In the case of a single hydrogel sheet, the electrodes and their respective overlying regions of gel can effectively be electrically separated from one other by rendering intervening sections of the hydrogel relatively non-conductive. This can be achieved during the manufacture of the hydrogel or by treating the hydrogel sheet with, for example, heated blades which selectively dry portions of the hydrogel sheet. In any event, whatever technique is used, the electrical resistance between adjacent electrodes should be high relative to the resistance via the gel between each electrode and the underlying tissue.

Generally, the more test electrodes in the array the better the resolution. The optimum number will depend on the given application, the size of the wound under study and the mapping accuracy required. A typical range is a rectangular array of from 5×5 to 100×100 electrodes depending on application and wound size. For certain routine clinical monitoring applications as few as two test electrodes may be sufficient. Typical test electrode sizes range from 1 mm×1 mm to 1 cm×1 cm. A range of electrode arrangements are possible for Impedance measurement. The best will depend on the given application.

Before describing the drive circuitry for the electrode array of FIGS. 7 and 8, several techniques for measuring the electrical characteristics of tissue will first be described.

If the same two electrodes are used to inject current and to measure the resultant voltage (or vice versa), this is termed the 2-electrode technique. In this case, the impedances of the two electrode-skin interfaces are measured in series with that of the underlying tissue between them.

A 4-electrode technique involves injecting current via a different pair of electrodes to those used to detect the voltage. In theory this avoids contributions from the four electrode-skin interfaces and one should therefore optimally observe the properties of the tissue between the voltage detecting electrodes.

A 3-electrode technique exists which enables one to study the properties of an individual interface without contributions from the other electrodes or the bulk of the sample. This technique is ideally suited to study the impedance of one single electrode-skin site.

Figure 6:
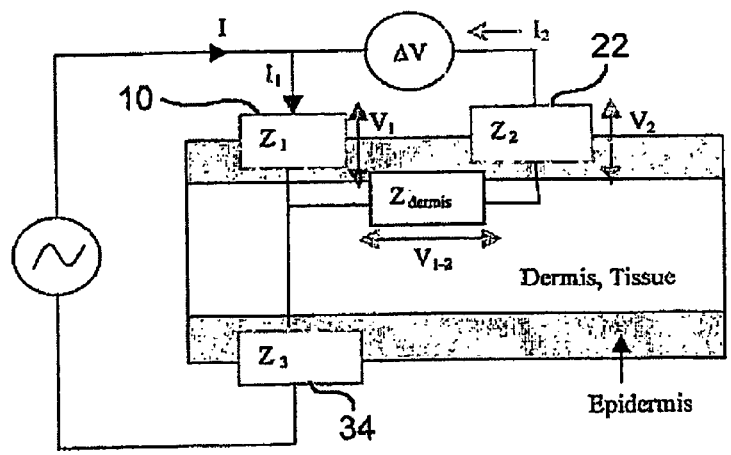
FIG. 6 is a schematic circuit diagram illustrating the impedance-measuring principle used in the present embodiment.

Based on the above, the electrode technique preferred for use in wound mapping in the present embodiment is the three electrode technique (FIG. 6). This involves the use of a test electrode 10 through which an alternating current is passed and a 'back' electrode 34, usually positioned on the opposite side of the body segment under investigation, to complete the current loop. A reference electrode 22 positioned directly beside the test electrode 10 effectively senses only the potential $V_1$ dropped across the electrode-skin impedance under test, $Z_1$.

The potential $\Delta V$ detected by the high input impedance voltmeter measures the following:

$$\Delta V = V_1 + V_{1-2} + V_2 = I_1 Z_1 + I_2 Z_{dermis} + I_2 Z_2 \quad (6)$$

As the voltmeter used contains an instrumentation amplifier with an extremely high input impedance, the current $I_2$ flowing through it (and the impedances $Z_{dermis}+Z_2$) will be negligibly small. The voltages $V_{1-2}$ and $V_2$ measured across the tissue impedance and the site below the reference electrode, respectively, will therefore also be negligible. As a result, the measured voltage difference $\Delta V$ is solely equal to the voltage drop Vacross the test electrode-skin impedance under investigation. The electrode-skin interface impedance $Z_1$ under study is simply obtained by dividing the measured voltage drop $\Delta V$ by the applied current I.

In the present embodiment, as shown in FIG. 7, a single reference electrode 22 is common to a plurality of test electrodes 10. This arrangement has the advantage of not requiring changes in connection to the reference electrodes while impedance measurements are carried out from one test electrode in the array to another. A further advantage is that the long fine amalgamation of the reference electrodes takes up less space on the electrode array, thus maximising the surface covered by test electrodes in the array. Although the back electrode 34 is generally best positioned on the opposite side of the body site under investigation, it can be incorporated into the array for ease of use. In this case it can be, for example, a long electrode screen printed on the substrate 18 around the peripheral edge of the array (not shown).

Figure 10:
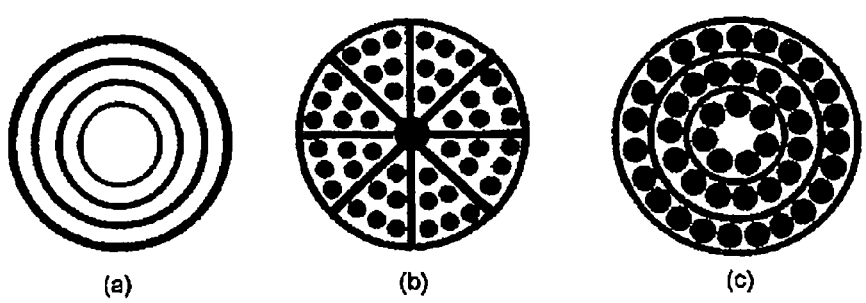
FIG. 10 illustrate alternative forms of test electrode arrays.

The test electrodes 10 forming the arrays may be rectangular, as in FIG. 7, circular or any other form which is best suited for a given application and which lends itself best to the fabrication technique. The distribution of the test electrodes in the arrays may be regular or irregular, as required by the given application and algorithms used. For example, the test and reference electrodes may be a series of concentric circles, FIG. 10a, or the test electrodes may be disposed between the "spokes" of a wheel-like reference electrode, FIG. 10(b). Alternatively the test electrodes may be disposed between concentric reference electrodes, FIG. 10(c). Obviously many permutations are possible. In FIG. 10 the leads to the test and reference electrodes are not shown for clarity. Connecting leads can be either be (i) interlaced around other electrodes, (ii) deposited in layers interspaced with dielectric insulating layers to enable the crossing over of the leads without electrical shorting or (iii) 'through-hole-plated' to the reverse side of the substrate so that the leads avoid the side with the deposited electrodes.

Referring now to FIG. 9, in use the 5×5 array of electrodes 10 is connected to a rotary switch 50 by a ribbon connector 52. The ribbon connector 52 has twenty-six conductors, one each connected individually to each of the twenty-five test electrodes 10 and one connected in common to all six reference electrodes 22. At the electrode array end the connection is made by a crimp connector 54 to the exposed ends of the leads 20, 28 at the substrate connector edge 26, while at the rotary switch the connection is made by a 26-way DIN connector 56. The rotary switch has two output lines 58 and 60. The former is permanently connected to the reference electrode lead 28. The latter is selectively connectable individually to any one of the test electrodes 10, according to the rotary position of the switch 50.

The lines 58, 60 are connected to respective inputs of an interface circuit 62, which also has an input from the back electrode 34. An Impedance analyser 64 is connected to the electrode array via the interface circuit 62 and the rotary switch 50. For each position of the switch 50 the impedance analyser 64 is actuated to generate an alternating test current and measure the resulting impedance of the tissue under the currently selected test electrode 10 according to the principles described with reference to FIG. 6. The impedance analyser 64 may comprise a Solartron 1260 Impedance/Gain Phase Analyser marketed by Solartron Analytical, Farnborough, Hampshire, England. The interface circuit 62 limits the test electrode current to acceptable levels in case of malfunction or inappropriate setting of the analyser 64.

The results of the analysis can be displayed directly as a wound map image on a video display device 66. In other words, the impedance values derived from the rectangular 5×5 (or other size) matrix of test electrodes 10 are displayed as corresponding colours, shades or numerical values on the device 66 in a similar matrix whose individual locations correspond to those of the electrode array. The results can alternatively or additionally be output on other forms of human-readable display devices, such as printers or plotters.

For each test electrode the measurement may be made at one AC frequency or measurements can be made at each of a plurality of frequencies, depending upon the application and output requirement. In general a suitable range of frequencies is from 1 milliHz to 100 kHz, preferably from 1 Hz to 50 kHz, although where a measurement is made at only a single frequency a value towards the lower end of the latter range is preferred.

As discussed, the test electrodes 10 may be used to apply iontophoretic or other therapeutic electrical signals to the wound. In that case a suitable therapeutic signal generator 68 is connected to the interface circuitry 62, and the latter contains switching circuits which switch over from the impedance analyser 64 to the signal generator 68 when it is desired to apply such therapy.

In a modification of the above embodiment, separate reference electrodes 22 are not used. Instead, during measurement on any selected test electrode 10 an adjacent test electrode acts temporarily as its reference electrode. Thus the particular test electrode acting temporarily as the reference electrode for any given test electrode undergoing measurement would be connected by the rotary switch 50 to the line 58 in FIG. 9.

An advantageous feature of the embodiment is the possible use of the 4-electrode technique by appropriate connection to sets of any four electrodes in the array. The 4-electrode technique enables the study of the underlying tissue Impedance and can be used to assess the tissue within the wound. Inter-electrode distances influence the depth the electric field penetrates into the tissue and hence these can be chosen to study differing depths of the wound. In electrode arrays incorporating many small area electrodes, combinations can be chosen to study and map the wound site for a range of penetration depths.

Obviously a suitably wide frequency range (typically from Megahertz to Millihertz) should be used and a sufficiently large number of data points obtained if a complete characterisation is required for research purposes. For routine clinical use of the invention, one or several strategically chosen frequency measurements may be all that is required for a given application. The applied signal amplitude for impedance measurement should be such as to ensure that the resultant current density is low, ensuring electrical safety and skin impedance linearity.

Figure 1:
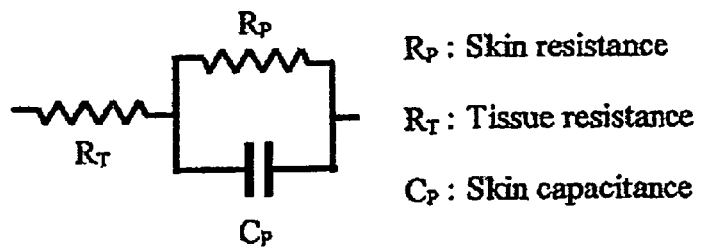
FIGS. 1 to 4 (previously described) are diagrams illustrating the electrical properties of the human skin.
Figure 2:
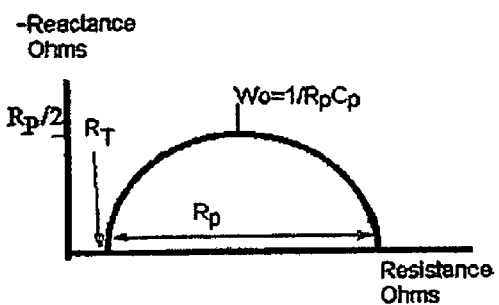
Figure 3:
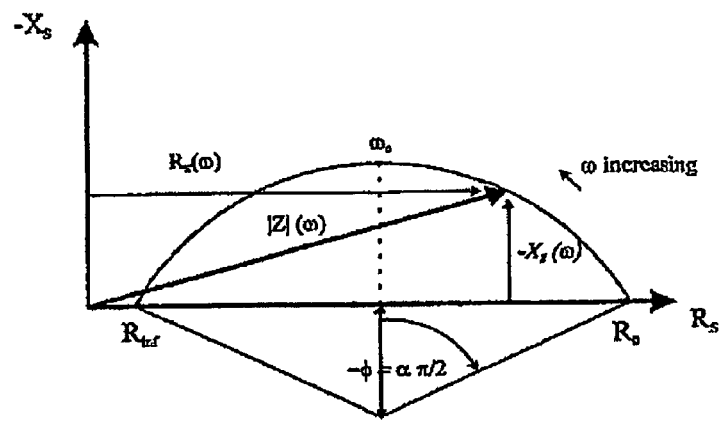
Figure 4:
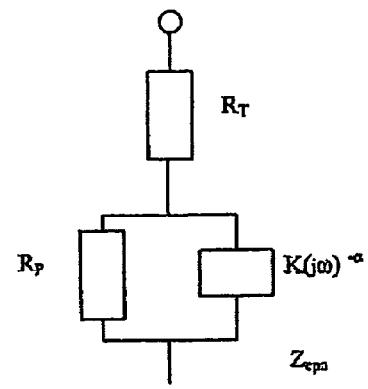
Figure 5:
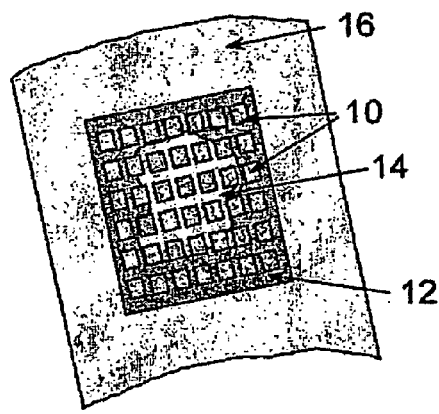
FIG. 5 (previously described) is a schematic diagram illustrating the general principles of an embodiment of the invention.

For research purposes, for example, to study the effects of electromagnetic fields on wound healing, one may be interested in measuring the skin or tissue impedances over a wide frequency range using numerous frequencies. Maps of the calculated parameters of mathematical models (e.g. Cole equation (equation 1)) or equivalent circuit models (e.g. FIG. 4) may then be presented on a monitor screen or printed for records. Alternatively, for example, the areas of specific regions as revealed by impedance parameters, ratios of parameters or other calculations involving such parameters may be calculated and presented, dispensing with the need to present, inspect and interpret maps.

Maps of calculations based on the following can be used to highlight difference regions in the wound site and differences in the tissues involved:
 (i) Magnitude of the impedance (or admittance or similar electrical property) (modulus, real and imaginary components) and phase angle measured at a given frequency.
 (ii) Ratios of the above where two or more such measurements are carried out at different frequencies. Other mathematical calculations are also possible.
 (iii) Mathematical model parameters (e.g. Cole model) and ratios or other mathematical calculations involving such parameters.
 (iv) Equivalent circuit parameters and ratios or other mathematical calculations involving such parameters.

For Intact skin, the impedance measured at a low frequency is dominated by the skin impedance rather than that of the underlying tissue. Maps of a wound site can therefore be simply obtained by mapping the site impedances measured at one single frequency, thus greatly simplifying the procedure.

If, based on research, only one model parameter is of interest for a given application, only two or three measurement frequency points will be required. For example, the calculation of K, a and Rp in the equivalent circuit model shown in FIG. 4 will require the use of at least two frequencies, more if high accuracy is required.

A suitably designed impedance array according to the preceding principles can be used to study the electrical properties of other organs/structures such as the heart or brain. Arrays of very small electrodes (e.g. in the micrometer range) can be fabricated using thin film techniques unto flexible substrates. In the case of the heart, areas of ischaemia may be detected, characterised and mapped using this invention.

The invention is not limited to the embodiments described herein and may be modified or varied without departing from the scope of the invention.

REFERENCES

1. Kantor, J., Margolis, D. J., 'Efficacy and Prognostic Value of Simple Wound Measurements', *Arch. Dermatol.* 1998; 134:1571-1574.
2. Langemo, D. K., Melland, H:, Hanson, D., Olson, B., Hunter, S., Henly, S. J.; 'Two-Dimensional Wound Measurement: Comparison of 4 Techniques', *Advances in Wound Care* 1998; 11:337-343.
3. CREST, Guidelines on the General Principles of Caring for Patients with Wounds, 1998.
4. S. Bale and V. Jones, Wound Care Nursing—A patient-centred approach: Bailliere Tindall, 1997.
5. www.naturesrain.com/theskin.htm, 1997.
6. Lackermeier, A. H., McAdams, E. T., Moss, G. P., Woolfson, A. D.; 'In vivo A. C. Impedance Spectroscopy of Human Skin: Theory and Problems in Monitoring of Passive Percutaneous Drug Delivery', *Annals of the New York Academy of Sciences* 1999; 873:197-213.
7. J. Jossinet and E. T. McAdams, "The Skin/Electrode Interface Impedance," *Innovation and Technology in Biology and Medicine*, vol. 12, pp. 22-31, 1991.
8. Lackermeier, A. H.; 'A novel multi-channel Impedance analyser for the in vivo investigation of the electrical properties of human skin during transdermal drug delivery', *Ph.D. Thesis* 2000.
9. McAdams, E. T., Jossinet, J.; 'The importance of electrode-skin impedance in high resolution electrocardiography', *Automedica* 1991; 13:187-208.

10. Cole, K. S.; 'Permeability and impermeability of cell membranes for ions', *Cold Spring Harbor Symp. Quant. Biol.* 1940; 8:110-112.
11. K. M. Bogie, S. I. Reger, S. P. Levine, and V. Sahgal, "Electrical stimulation for pressure sore prevention and wound healing," *Assistive Technology*, vol. 12, pp. 50-66, 2000.
12. G. D. Mulder, "Treatment of Open-Skin Wounds with Electric-Stimulation," *Archives of Physical Medicine and Rehabilitation*, vol. 72, pp. 375-377, 1991.
13. S. I. Reger, A. Hyodo, S. Negami, H. E. Kambic, and V. Sahgal, "Experimental wound healing with electrical stimulation," *Artificial Organs*, vol. 23, pp. 460-462, 1999.

The invention claimed is:

1. A system for monitoring surface changes in a skin wound over time, the system comprising:
   a wound dressing including a two-dimensional array of test electrodes for application to the surface of the wound,
   a circuit electrically coupled to the two-dimensional array of test electrodes, the circuit for measuring an electrical characteristic of tissue immediately underlying each test electrode, said circuit comprising:
      a switching device for selecting successive test electrodes, and
      an analyser for passing an electrical alternating current between each selected test electrode and at least one further electrode applied to the skin at a location away from the wound,
         said analyser further calculating the electrical characteristic of the tissue immediately under each currently selected test electrode as a function of the voltage difference between the currently selected test electrode and at least one reference electrode, adjacent to the currently selected test electrode, the voltage difference being measured while passing the electrical alternating current between each currently selected test electrode and the at least one further electrode; and
   a display device electrically coupled to the analyser, the display device for presenting a visual map generated using analyser circuitry of said analyser, the map indicating the size and shape of the wound based upon the measured electrical characteristic.

2. A system as claimed in claim 1, wherein the array of test electrodes is arranged on a flexible backing of insulating material.

3. A system as claimed in claim 2, wherein the further electrode is disposed on the flexible backing of insulating material.

4. A system as claimed in claim 2, wherein the array of electrodes is a rectangular array.

5. A system as claimed in claim 2, wherein each test electrode is covered with a conductive gel, the resistance between adjacent test electrodes being high relative to the resistance via the gel between each test electrode and the underlying tissue.

6. A system as claimed in claim 5, wherein the gel is a hydrogel.

7. A system as claimed in claim 2, wherein leads for the test electrodes are also disposed on the flexible backing of insulating material and covered with an insulating material.

8. A system as claimed in claim 1, wherein the two-dimensional array comprises at least 25 test electrodes.

9. A system as claimed in claim 1, wherein the electrical characteristic is an impedance of the tissue immediately underlying each test electrode.

10. A system as claimed in claim 1, wherein for each test electrode a measurement is made at a plurality of different frequencies.

11. A system as claimed in claim 1, wherein each measurement is made at a frequency of from 1 milliHz to 100 kHz.

12. A system as claimed in claim 1, wherein said switching device for selecting successive test electrodes also selects, for the currently selected test electrode, at least one test electrode, adjacent to the currently selected test electrode to act temporarily as said reference electrode with respect to the currently selected test electrode.

13. A system as claimed in claim 2, wherein said at least one reference electrode is a dedicated electrode on the flexible backing of insulating material.

14. A method of monitoring surface changes in a skin wound over time, the method comprising:
   applying a dressing to the wound, the dressing including a two-dimensional array of test electrodes applied to the surface of the wound;
   measuring an electrical characteristic of tissue immediately underlying each test electrode by selecting successive test electrodes, passing an electrical alternating current between each selected test electrode and a further electrode applied to the skin at a location away from the wound, and calculating the electrical characteristic of the tissue immediately under each currently selected test electrode as a function of the voltage difference between the currently selected test electrode and at least one reference electrode adjacent to the currently selected test electrode, the voltage difference being measured while passing the electrical alternating current between each currently selected test electrode and the at least one further electrode; and
   presenting a visual map indicating the size and shape of the wound based upon the measured electrical characteristic.

15. A method as claimed in claim 14, wherein the array of test electrodes is arranged on a flexible backing of insulating material.

16. A method as claimed in claim 15, wherein each test electrode is covered with a conductive gel, the resistance between adjacent test electrodes being high relative to the resistance via the gel between each test electrode and the underlying tissue.

17. A method as claimed in claim 14, wherein the two-dimensional array comprises at least 25 test electrodes.

18. A method as claimed in claim 14, wherein the electrical characteristic is the impedance of the tissue immediately underlying each test electrode.

19. A method as claimed in claim 14, comprising, for each currently selected test electrode, selecting at least one test electrode adjacent to said currently selected test electrode to act temporarily as said reference electrode with respect to the currently selected test electrode.

20. A system as claimed in claim 15, wherein said at least one reference electrode is a dedicated electrode on the flexible backing of insulating material.

* * * * *